United States Patent [19]

Laughlin

[11] 4,420,329
[45] Dec. 13, 1983

[54] STABLE COLLOIDAL DISPERSIONS OF TRIACONTANOL

[75] Inventor: Robert G. Laughlin, Cincinnati, Ohio

[73] Assignee: The Procter & Gamble Company, Cincinnati, Ohio

[21] Appl. No.: 319,565

[22] Filed: Nov. 9, 1981

Related U.S. Application Data

[63] Continuation-in-part of Ser. No. 273,524, Jun. 15, 1981, abandoned.

[51] Int. Cl.$^3$ .............................................. A01N 31/02
[52] U.S. Cl. .................................. 71/122; 71/DIG. 1
[58] Field of Search ........................... 71/122, DIG. 1

[56] References Cited

U.S. PATENT DOCUMENTS

| | | | |
|---|---|---|---|
| 4,146,499 | 3/1979 | Rosano | 252/186.32 |
| 4,150,970 | 4/1979 | Ries et al. | 71/122 |
| 4,157,982 | 6/1979 | Clemons et al. | 252/311 |
| 4,230,485 | 10/1980 | Ohlrogge | 71/122 |
| 4,333,759 | 6/1982 | Welebir | 71/80 |

FOREIGN PATENT DOCUMENTS 1308156  2/1973  United Kingdom .

OTHER PUBLICATIONS

Farm Chemicals, 141:42–46 (1978).
Jones, et al., Planta, 144:277–282 (1979).
Maugh, Science, 212:33–34 (1981).
Ries, et al., J. Amer. Soc. Hort. Sci., 103 (3):361–364 (1978).
Hoagland, Bot. Gaz., 141(1):53–55 (1980).
Bouwkamp, et al., HortScience, 15(1):69 (1980).
Bosland, et al., HortScience, 14(6):729–730 (1979).
Folger, *Sonochemical Engineering*, 67(109):1–12 (1971).
Prakash, et al., *Ultrasonics and Colloids*, 33–48 (1961).
Reddy, et al., Journal of Colloid and Interface Science, 79:101–104 (1981).

*Primary Examiner*—Catherine L. Mills
*Attorney, Agent, or Firm*—Jacobus C. Rasser; Donald E. Hasse; Steven J. Goldstein

[57] ABSTRACT

Stable colloidal dispersions of 1-triacontanol in water are disclosed. The dispersions are capable of more consistently stimulating plant growth by allowing for the uniform application of a large number of very small crystalline triacontanol particles. The dispersions preferably also contain an anionic, cationic, zwitterionic or polyfunctional single bond nonionic surfactant dispersing agent.

25 Claims, No Drawings

STABLE COLLOIDAL DISPERSIONS OF TRIACONTANOL

This application is a continuation-in-part of application Ser. No. 273,524, filed June 15, 1981, now abandoned.

TECHNICAL FIELD

The present invention relates to stable colloidal dispersions of 1-triacontanol (hereinafter referred to as triacontanol) in water. Triacontanol, a $C_{30}$ linear, primary alcohol, occurs in nature and can be extracted from alfalfa as a crystalline product. It is known in the art to be useful for stimulating growth in a wide variety of plants, including agricultural crops such as corn, soybeans, wheat, rice and tomatoes. However, field testing of various triacontanol formulations has generally produced inconsistent and disappointing results. The stable colloidal dispersions herein are capable of more consistently stimulating plant growth because they allow for the uniform application of a large number of very small crystalline triacontanol particles.

BACKGROUND ART

U.S. Pat. No. 4,150,970, Ries et al., issued Apr. 24, 1979, discloses the use of triacontanol to stimulate plant growth. Formulations are prepared by dissolving the triacontanol in organic solvents such as chloroform or benzene and then adding the solution to water, which can also contain an emulsifying agent.

Farm Chemicals, 141:42-46 (1978), discloses that triacontanol significantly increased yields of several crops in limited field testing. However, broad-scale testing is said to be needed in view of the difficulty in finding plant biostimulants consistently effective under practical conditions.

Jones, et al., Planta, 144:277-282 (1979), report that various analogs of triacontanol differing in carbon chain length, position of the hydroxyl group and identity of the terminal functional group all failed to stimulate plant growth, and actually inhibited triacontanol's activity when applied with it. The authors conclude that triacontanol should be free of trace amounts of other long-chain compounds, particularly 1-octacosanol, for effective plant growth stimulation.

U.S. Pat. No. 4,230,485, Ohlrogge, issued Oct. 28, 1980, describes the application of triacontanol to corn plants after tassel initiation to improve yields. The formulations are preferably prepared by dissolving triacontanol in acetone and then mixing the solution with water.

Maugh, Science, 212:33-34 (1981), reports that field testing of triacontanol has proven disappointing and caused many investigators to give up on the compound. Ries is said to attribute most of the problems to inadequate methods of formulation. Welebir is said to think that activity is also related to metal ion concentration and pH.

While triacontanol is known to be useful for stimulating plant growth, it is apparent that there is a continuing need for triacontanol formulations capable of more consistently stimulating growth under practical conditions.

SUMMARY OF THE INVENTION

The present invention encompasses stable colloidal dispersions comprising: (a) from about $10^{-10}$ g/l to about 0.5 g/l of 1-triacontanol having a mean particle radius of less than about 0.3 microns, and (b) water.

The invention also encompasses stable colloidal dispersions comprising: (a) from about $10^{-10}$ g/l to about 4 g/l of 1-triacontanol having a mean particle radius of less than about 0.3 microns, (b) a dispersing agent selected from the group consisting of anionic, cationic, zwitterionic and polyfunctional single bond nonionic surfactants, wherein the dispersing agent is present at a concentration of less than about 50% by weight of the 1-triacontanol and, additionally, is present at a concentration less than its critical micelle concentration when it has a hydrocarbyl chain length of less than or equal to about 18 carbon atoms, and (c) water.

Methods for preparing the above dispersions of triacontanol and methods for stimulating plant growth by applying thereto effective amounts of the dispersions are also part of the present invention.

DETAILED DESCRIPTION OF THE INVENTION

The stable colloidal dispersions of the present invention allow for the uniform application of a large number of very small crystalline triacontanol particles, and thus are capable of more consistently stimulating plant growth than are the triacontanol formulations disclosed in the art.

It is believed that previous formulations have often been prepared by dissolving the triacontanol in an organic solvent such as chloroform, acetone or Tween 20. The solutions are then mixed with water, which can also contain an emulsifying agent, to precipitate triacontanol particles. Such formulations, while producing a certain amount of colloidal triacontanol particles, typically result in a large mean particle size (e.g., a mean particle radius of at least several microns) and a correspondingly small particle number concentration. A significant, but ill-defined, fraction of the triacontanol precipitates as large particles which undergo rapid flocculation. These formulations therefore provide relatively poor uniformity of application in the field.

Other formulations have been prepared by dissolving the triacontanol in a water-insoluble solvent (e.g., naptha) and then emulsifying with water in the presence of an emulsifying agent. In these formulations, the triacontanol remains dissolved in the solvent where it has low chemical and biological activity. Since the particle number concentration of the dispersed triacontanol solution will be small, field applications will also be relatively nonuniform. In addition, the mixing of the triacontanol solutions with water in both of the above described methods typically occurs just prior to field applications so that the triacontanol particle size and particle number concentration, and hence uniformity of application, are not known or controlled.

In contrast with previous triacontanol formulations, the dispersions herein have a very small triacontanol particle size, which insures good colloidal stability, and a very large particle number concentration. For example, a dispersion of 1 g/l of 0.1 micron radius particles would contain about $3 \times 10^{15}$ particles/l, assuming that the particles are monodisperse, spherical and have a density of 0.82 g/cc. After dilution with water to $10^{-6}$ g/l, the particle number concentration would be $3 \times 10^9$/l. Since 200 micron diameter spray droplets encountered in agricultural sprays contain about $4.2 \times 10^{-9}$ l, each droplet would contain about 12 triacontanol particles, on average. Because the particle number concentration decreases as the cube of the particle radius (keeping the chemical composition constant), it can be seen that if the particle radius is much larger than 0.1 micron, many droplets would contain no triacontanol particles at all at $10^{-6}$ g/l. Using the above assumptions, if the particle radius is 1 micron, then only about one droplet in 100 would contain a triacontanol particle.

The dispersions of the present invention are initially prepared in the laboratory or plant where the colloidal dimensions (i.e., particle size and number concentration) can be easily measured and controlled. Once formed, the dispersions appear to be indefinitely stable (samples stored at room temperature for a period of 8 months have not flocculated and appear to be unchanged). For practical and economical reasons, the dispersions herein will typically be prepared in concentrated form and will then be diluted with water just prior to use to provide a spray solution, nutrient broth, etc. Importantly, dilution of the concentrated dispersions does not alter their colloidal dimensions. And since the triacontanol particles are not surface active, the dilution factor can be very large without loss of material to container surfaces or the air-water interface. Finally, the dispersions herein provide crystalline triacontanol particles which have optimum chemical and biological activity and are readily available to the plants because they remain dispersed in the aqueous plant vascular fluids. Due to their small size, the mobility of the triacontanol particles within such aqueous systems is reasonably high (e.g., the mean diffusion coefficient of particles in the dispersions is between $10^{-7}$ and $10^{-8}$ $cm^2\ sec.^{-1}$).

The stability of the present dispersions is determined, in part, by the size of the dispersed triacontanol particles. Particle size is determined herein by a cumulant analysis of the autocorrelation function obtained in a quasi-elastic (dynamic) light scattering (QELS) measurement. QELS is described by Berne and Pecora in *Dynamic Light Scattering, J. Wiley & Sons (*1976), incorporated herein by reference. The cumulant analysis for interpreting QELS data for polydisperse systems is described in Chapter 8 of the above reference and by Koppel in J. Chem. Physics, 57:4814 (1972), incorporated herein by reference. All QELS measurements herein are obtained using a Malvern homodyne spectrometer and a 96 channel autocorrelator to determine the correlation function. The particles are illuminated with light from a helium-neon laser operating at a wavelength of 6328 Å, and the scattered light is observed at a scattering angle of 90°. Sample times are from $1\times10^{-5}$ to $5\times10^{-5}$ seconds, such that the correlation function decays to from 1/10th to 1/20th of its original value. The sample temperatures are controlled, and literature values for the corresponding viscosity and refractive index of water at the controlled temperature are used in computing the particle size. The particle size distributions are obtained from a cumulant analysis, of degree either 2 or 3, of the autocorrelation function by assuming the particles are spherical and obey Stokes-Einstein dynamics. There is, therefore, no kurtosis assumed in the distribution. Both a mean particle radius, r, and a value for the breadth of the distribution, δr, result from the analysis. (The term "means particle radius" is used herein instead of the more accurate term "mean equivalent hydrodynamic radius", which is the mean apparent radius calculated from an experimentally determined diffusion coefficient, assuming spherical particles. δr as used herein is the standard deviation of the radius about r, assuming the particle size distribution is gaussian.)

For acceptable stability of the present dispersions (i.e., little or no flocculation), the triacontanol particles must have a mean particle radius of less than about 0.3 microns. The mean particle radius is preferably less than about 0.25 microns, and more preferably less than about 0.15 microns, for greatest stability and highest particle number concentration. For dispersions prepared by sonication as hereinafter described, δr/r typically ranges from about 0.4 to about 0.55. However, dispersions having acceptable stability can be obtained at values for δr/r up to about 0.8. At higher values, the particle size distribution would be large enough that a significant fraction of the triacontanol particles would flocculate. There is, of course, no critical lower limit on the value for δr/r since monodisperse systems, if they could be prepared, would be useful.

The stability of the dispersions herein is also determined, in part, by the amount of the triacontanol present. Substantially complete dispersion of triacontanol in water can be obtained at levels up to about 0.5 g/l of triacontanol. At higher levels, partial dispersion will occur but a significant, readily apparent, fraction will flocculate. It is believed that plant growth stimulation can be obtained, at typical application rates, at levels down to about $10^{-10}$ g/l of triacontanol. Thus, the present invention provides stable colloidal dispersions containing water and from about $10^{-10}$ to about 0.5 g/l, preferably from about $10^{-8}$ to about 0.4 g/l, and more preferably from about $10^{-5}$ to about 0.25 g/l, of triacontanol. If the concentration of triacontanol exceeds about 0.5 g/l, a dispersing agent is required to prevent excessive flocculation. However, even with the dispersing agent present, a significant fraction of the triacontanol flocculates if its concentration exceeds about 4 g/l. Thus, the present invention also provides stable colloidal dispersions containing water, from about $10^{-10}$ to about 4 g/l, preferably from about $10^{-8}$ to about 3 g/l, more preferably from about $10^{-5}$ to about 1.5 g/l, of triacontanol and a dispersing agent. The dispersing agent is a preferred component for processing and handling reasons since it allows for the preparation of more concentrated dispersions (e.g., 1 g/l of triacontanol) which can then be diluted with water or other suitable media (e.g., the anti-freeze materials hereinafter described) to the desired triacontanol concentration prior to application. In addition, the use of a dispersing agent provides a significantly smaller mean particle size and higher particle number concentration at a given level of triacontanol.

The dispersing agent can be any anionic, cationic, zwitterionic or polyfunctional single bond nonionic surfactant (semipolar nonionic surfactants are not useful herein). These surfactants are described by Laughlin in *Advances in Liquid Crystals,* Vol. 3, G. H. Brown (ed.), 1978, particularly from pages 61-66, incorporated herein by reference. The phrase "polyfunctional single bond nonionic surfactant" includes the polyoxyethylene nonionics, polyol sugar monoesters, and the like. Amphiphilic structures, in which the polar, water-binding, hydrophilic group contains only hydroxyl and/or ether functional groups, must contain a multiplicity of these functional groups to be operative as surfactants. The monohydroxy and monoether structures are not operative as surfactants, as defined by Laughlin in the above reference. Suitable surfactant dispersing agents are also described in U.S. Pat. No. 3,929,678, Laughlin et al., issued Dec. 30, 1975, incorporated herein by reference.

Preferred dispersing agents herein have sufficiently high Krafft boundaries (e.g., greater than about 10° C. above the application temperature) that they will not form potentially phytotoxic concentrated surfactant solutions upon evaporation of aerosol sprays containing the dispersions. The most preferred dispersing agents herein are the sodium or potassium $C_{14}$-$C_{24}$ alkyl sulfates, alkyl ether ethoxylate sulfates containing less than about 2 ethylene oxide units, alkyl glyceryl ether sulfonates and fatty acid soaps. An especially preferred dispersing agent is sodium tallow alkyl sulfate.

The dispersing agent can be present at a concentration less than about 50%, preferably less than about 20%, more preferably less than about 2%, by weight of the triacontanol. Additionally, if the dispersing agent has a hydrocarbyl chain length of less than or equal to about 18 carbon atoms, it must be present at a concentration less than its critical micelle concentration (cmc) to prevent the micellar solubilization of the triacontanol. Micellar solutions of triacontanol are undesirable because they reduce the activity of the triacontanol, decrease the colloidal stability of the dispersion and precipitate relatively large triacontanol particles upon dilution. Such a dispersing agent is preferably present at a concentration less than about 0.25, preferably less than about 0.1, times its cmc. If the dispersing agent has a hydrocarbyl chain length of greater than about 18 carbon atoms, it generally must be used at a total concentration greater than its cmc in order to provide an adequate surface concentration to achieve colloid stability. (Because such long-chain surfactants are efficiently adsorbed at the particle/water interface, their solution concentration will usually be reduced to a value near or below their cmc). Within the above limits, it is generally preferred that the dispersing agent be used at its lowest effective level for stabilizing the dispersion since it can sometimes inhibit the growth stimulation benefits provided by triacontanol.

It will be appreciated that since neither the triacontanol nor many of the longer-chain dispersing agents herein are significantly water-soluble at room temperature or below, the present aqueous dispersions will freeze over a very narrow temperature range. Freezing of the dispersions forces the colloidal triacontanol particles together and enhances flocculation. Thus, as a preferred component useful for imparting freeze-thaw stability, the present dispersions can additionally contain up to about 40%, preferably from about 10% to about 25%, by weight of an anti-freeze material. Suitable anti-freeze materials include, for example, water-soluble alcohols such as methanol or ethanol, dipolar aprotic solvents such as dimethyl sulfoxide, and polyols such as ethylene glycol, propylene glycol, diethylene glycol, glycerol, erythritol, pentaerythritol, xylitol, and the various sugar alcohols. The anti-freeze material is preferably propylene glycol, glycerol, sorbitol or mixtures thereof, and most preferably is propylene glycol.

The stable colloidal dispersions of the present invention can be prepared by sonicating a mixture of the components (i.e., triacontanol, water, and optionally the dispersing agent and/or antifreeze material) at a temperature above the melting point of the triacontanol (ca. 90° C.) until a stable colloidal dispersion is formed, and then cooling the dispersion produced to a temperature less than the melting point of the triacontanol. The triacontanol must be heated to above its melting point to be effectively dispersed. However, because the severe mechanical energy input provided by sonication can create significant temperature gradients within the system, the mean temperature can vary slightly (e.g., 5° C.) below the melting point while still providing dispersion. Sonication is generally described by Prakash, et al. in *Ultrasonics and Colloids*, University of allahabad, India (1961); in *Sonichemical Engineering*, American Institute of Chemical Engineers, H. S. Folger, (ed.), (1971); and by Reddy, et al. in the Journal of Colloid and Interface Science, 79:105-113 (1981), all incorporated herein by reference.

While not intending to be limited by theory, it is believed that sonication disperses the liquid triacontanol into extremely small particles by cavitation. The final triacontanol particle size is determined by the size distribution initially formed, which is influenced by the sonication conditions (i.e., time, wattage and number of cycles in continuous sonication), and by the rate of coalescence of the particles outside the cavitation zone. The coalescence rate is predictably decreased by dilution of the formulation to be dispersed, since there will be fewer triacontanol particles per unit volume of solution to coalesce, and by adsorption of the dispersing agent at the triacontanol/water interface. The dispersing agent creates an additional barrier to coalescence which is probably electrostatic in nature when the dispersing agent is an ionic or zwitterionic surfactant, and is possibly steric in nature when the dispersing agent is a polyfunctional single bond nonionic surfactant. It is believed that the semipolar surfactants (e.g., amine oxides, phosphine oxides) are not effective dispersing agents because they are small, weakly polar nonionics not capable of stabilizing colloids by the steric mechanism. The stabilization of colloids by electrostatic and steric mechanisms is described by Ottewill in *Nonionic Surfactants*, M. J. Schick (ed.), Ch. 19 (1967), incorporated herein by reference.

The present invention also encompasses methods for stimulating plant growth by applying thereto an effective amount of the stable colloidal dispersions herein. The mode of application to plants can be by any convenient form, such as by seed soaking, dipping, foliar spraying, soil drenching, or the addition of the dispersion to irrigation water or a nutrient solution. The time of application can also vary considerably in that the dispersion can be applied to seeds, seedlings or the leaves or roots of growing plants. While the optimum application rate will vary depending on the mode of application, it is believed that when spraying plants to the drip point the optimum triacontanol concentration ranges from about $10^{-8}$ to about $10^{-6}$ g/l. When spraying plants in the field, the spray generally should contain from about $10^{-8}$ to about $10^{-3}$ g/l, preferably from about $10^{-7}$ to about $10^{-4}$ g/l, of triacontanol. The dispersion is preferably applied in the field at a rate which provides from about $10^{-6}$ to about 1 g/ha, more preferably from about $10^{-5}$ to about $10^{-2}$ g/ha, of triacontanol.

As disclosed in the Jones, et al. reference, the purity of the triacontanol can significantly affect its ability to stimulate plant growth. The triacontanol used herein is preferably greater than about 97% pure, and more preferably greater than about 99% pure. Triacontanol of acceptable purity can be synthesized by the process described in U.S. Pat. No. 4,268,697, Gibson, issued May 19, 1981, particularly in column 3, lines 54-59, incorporated herein by reference.

As previously mentioned, the dispersions herein are useful for stimulating growth in a wide variety of plants. They are especially valuable for increasing yields in agricultural crops such as corn, soybeans, wheat, milo, rice, tobacco and cotton, and in truck crops such as tomatoes, asparagus, lettuce, beans and the like. The dispersions should also be useful for stimulating growth in trees, herbs, flowers and houseplants.

The following non-limiting examples illustrate the compositions and methods of the present invention.

All percentages, parts, and ratios used herein are by weight unless otherwise specified.

EXAMPLE I

A stable colloidal dispersion of triacontanol was prepared by batch sonication as follows.

Apparatus: A Heat Systems—Ultrasonics, Inc. Sonifier—Cell Disruptor, Model W185, with a stepped titanium microtip (0.32 cm tip diameter) was used. The 25 ml sonication vessel was conical, but with a flattened bottom, and contained a thermistor well flush against the side. It was connected by a spherical joint (unlubricated) to a short condenser having a threaded Teflon cap. The cap had an O-ring fitted hole through which the wide upper part of the sonication horn could be inserted. During use, the tip was 1–2 mm from the bottom of the vessel.

Procedure: Ten ml of distilled water, 10 mg of triacontanol (mp 89°–90° C., g.c. analysis: 97.3% 1-triacontanol, 2.2% 1-nonacosanol, and 0.5% 1-octacosanol), and 0.100 ml of sodium tallow alkyl sulfate (TAS) (recrystallized commercial sample containing 3.8% $C_{14}$, 27.9% $C_{16}$, and 63.2% $C_{18}$ homologs) stock solution (1 mg/ml), heated to dissolution prior to use, were placed in the sonication vessel. The condenser (with cooling water) was attached, the tip inserted, and the thermistor of a digital thermistor thermometer inserted in the well. The sample was heated to about 60° C. using an oil bath maintained at 85° C., at which point the sonifier was turned on. The power setting was adjusted to ca. 40 watts. The sonification rapidly brought the temperature to 90°–92° C.; it was held there, by adjusting depth of immersion in the bath, for a period of five minutes. The original high turbidity decreased during this period to the point that the tip became clearly visible. The vessel was then immersed in a beaker of water, dropping the temperature rapidly to ca. 65° C., at which point the sonifier was turned off.

After removing the tip, the condensate on the condenser walls was rinsed back into the vessel using a Pasteur pipette and the contents of the vessel. The condenser was then removed and the product, a uniformly hazy dispersion, decanted into a storage vial. The triacontanol had a mean particle radius r of about 0.215 microns and a δr of about 0.103 microns.

EXAMPLE II

A stable colloidal dispersion of triacontanol was prepared by continuous sonication as follows.

Apparatus: A Branson Sonifier Cell Disruptor, Model 350, with a Heat System-Ultransonics Cat. No. 200, 1.27 cm disruptor horn and Model 800B Continuous Flow Cell (stainless steel) was used. The cell was modified by replacing the stainless orifice plate with a teflon plate (0.16 cm hole) and by replacing the O-ring under the plate and the O-ring which sealed the orifice holder to the body tube with machined Teflon gaskets. After performing these modifications and passivating the cell by sonifying 0.01 N $H_2SO_4$ in the cell at 90° C., pure water could be recirculated through the cell without apparent change in turbidity. The original O-ring seal between the body tube and the thick upper part of the disruptor horn was left intact.

The sample port near the orifice plate was fitted so that a stainless steel jacketed thermistor probe could be sealed in this port. The thermistor was inserted to a point near but not touching the horn.

The chamber volume of the flow cell was 62 ml.

An FMI valveless reciprocating piston metering pump (FMI Model #RP-G150-1-CSC) fitted on the outlet with a tee holding a 4–5 cm sealed glass header tube and a needle valve was used to meter the dispersions through the flow cell. By adjusting the needle valve so that a back pressure of 1–2 atmospheres developed in the header, the pump surge was effectively eliminated. The outlet was connected to the flow cell sample port remote from the orifice plate using 0.16 cm CTFE tubing and stainless ferrule fittings; the pump inlet was similarly connected to the reservoir container.

During continuous sonication the flow cell was mounted with the orifice plate up. By pumping the stock dispersion into the lower sample port, air was completely displaced from the chamber. The sonication efficiency of this configuration was significantly higher than that of the inverted configuration with orifice plate down. A 50 cm length of 0.32 cm stainless steel tubing was connected to the outlet port; the tip was bent into a hook. This tube served as an air-bath exchanger which rapidly cooled the product exiting from the cell, and to generate a small hydrostatic pressure head. As the sonication occurred at 90°–91° C., close to the boiling point of water, the added hydrostatic pressure can also be expected to promote effective sonication.

Procedure: Four hundred mg of triacontanol, 400 ml water, and 0.400 ml of TAS dispersion (10 mg/ml) were placed in a 500 ml beaker with a star magnetic stirrer head. A jacketed thermistor sensor and the 1.27 cm disruptor horn were immersed in the liquid. The beaker was heated with stirring to 85° C., at which point the sonifier was turned on at full power (85 watts). Sonication was terminated when the temperature reached 95° C. The resulting coarse dispersion was white and apparently uniform. Six identical batches were prepared and were combined in a large conical flask. The flask was continuously stirred using a star magnetic stirrer head.

The titanium tip was removed and polished using fine emery cloth on a flat surface until smooth. It was weighed before and after sonication of the six batches. The customary pitting in a zone parallel to the edge of the tip and about 1 mm in was observed, but the weight loss was less than 1 mg. It was repolished prior to each continuous sonication run.

Continuous sonication was performed by pumping the coarse dispersion through the cell at a nominal rate of 10 ml/minute, keeping the cell temperature between 90°–91° C. The first 130 ml (ca. two chamber volumes) were remixed with the coarse dispersion before collection commenced. Then nine 250 ml aliquots were collected over a period of 218 minutes (10.3 ml/min). Turbidity readings were taken using a Bausch & Lomb Spectronic 20 set at 580 microns and a 1 cm cell. The approximate mean particle radii, inferred from other data on turbidity versus mean particle radius, were as follows.

| Fraction | Absorbance | r, microns |
|---|---|---|
| A | 0.330 | 0.185 |
| B | 0.378 | 0.190 |
| C | 0.380 | 0.190 |
| D | 0.415 | 0.196 |
| E | 0.398 | 0.195 |
| F | 0.387 | 0.194 |
| G | 0.394 | 0.195 |
| H | 0.420 | 0.198 |
| I | 0.430 | 0.199 |
| Cell holdup | 0.442 | 0.200 |

These data suggested that the product was relatively uniform. However, to reduce the particle size to a more preferred range, the combined fractions were resonicated as above, collecting 2100 ml in 205 minutes (10.2 ml/min). The chamber contents were added to the product to yield 2160 ml of a stable dispersion of triacontanol. The dispersion contained 927±27 mg/l of triacontanol and 12.6±0.4 mg/l of TAS. The triacontanol had a mean particle radius, r, of about 0.105 microns and a δr of about 0.059 microns.

The above dispersion can then be diluted with water to a triacontanol concentration of about $10^{-3}$ g/l and distributed to the ultimate user. After again being diluted with water to a concentration of about $10^{-6}$ g/l, the dispersion can be sprayed onto plants in the field at a rate of about 100 l/ha to provide sufficient triacontanol (about $10^{-4}$ g/ha) to stimulate plant growth and crop yields. Similar results can be obtained when the dispersion is applied at rates which provide about $10^{-5}$ or $10^{-3}$ g/ha of triacontanol.

Other dispersions of the present invention can be prepared by the methods described in Examples I and II when the sodium tallow alkyl sulfate is replaced with sodium eicosyl ethoxylate (2 avg.) sulfate, potassium tallow alkyl glyceryl ether sulfonate, sodium stearate, sodium $C_{12}$ linear alkylbenzene sulfonate, cetyl trimethylammonium bromide, 3-(N,N-dimethyl-N-coconutalkylammonio)-2-hydroxypropane-1-sulfonate, 2-trimethyl-ammoniohexadecanoate, N-tallow alkyl-N,N-dimethylammonioacetate, the condensation product of a $C_{10}$ linear aliphatic alcohol with about 5 moles of ethylene oxide, the condensation product of a $C_9$ linear alkyl phenol with about 9.5 moles of ethylene oxide, or with tallow acyl sorbitol polyethoxylate (10 avg.).

Other dispersions herein can be prepared by the methods described in Examples I and II when the concentration of triacontanol is about $10^{-1}$ g/l or 3 g/l, or when the weight ratio of triacontanol to dispersant is about 1000:1 or 100:1.

Dispersions of the present invention can also be prepared by the above methods when the concentration of triacontanol in water is about $10^{-2}$ g/l, 0.1 g/l or 0.4 g/l and no dispersant is present.

The addition of about 15% by weight of propylene glycol or sorbitol to the above dispersions enhances their freeze-thaw stability.

EXAMPLE III

The following dispersions of triacontanol in distilled water, both with and without sodium tallow alkyl sulfate (TAS), were prepared using batch sonication techniques as described in Example I.

| Sample No. | Triacontanol (g/l) | TAS (g/l) | Observations |
|---|---|---|---|
| 1 | 0.1000 | 0 | Stable, nearly water-clear colloid |
| 2 | 0.215 | 0 | Stable, moderately turbid colloid, similar to sample No. 6 |
| 3 | 0.464 | 0 | Stable, nearly opaque colloid, few large particles |
| 4 | 1.000 | 0 | Flocculated immediately when quenched to 75° C. |
| 5 | 1.000 | 0.010 | Stable, moderately turbid colloid |
| 6 | 2.154 | 0.0215 | Stable, nearly opaque colloid |
| 7 | 4.642 | 0.0464 | Flocculated on standing |

These data suggest that stable colloidal dispersions can be prepared at triacontanol concentrations up to about 0.5 g/l without the dispersant TAS, and at concentrations up to about 4 g/l with TAS present.

EXAMPLE IV

Triacontanol was dissolved in acetone, Tween 20 and Tween 80 at concentrations of 1000 mg/l. The solutions were then poured into distilled water to form the indicated concentrations of triacontanol. None of the samples were completely dispersed; all displayed visible flocculation. The mean particle radius, r, and δr were determined as follows.

| Sample No. | Solvent | Concentration (mg/l) | Diluted Concentration (mg/l) | r (microns) | δr |
|---|---|---|---|---|---|
| 1 | Acetone | 1000 | 100 | — | — |
| 2 | Acetone | 1000 | 10 | — | — |
| 3 | Acetone | 1000 | 1 | 16.8 | 6.8* |
|   |         |      |   | 10.0 | 5.4* |
| 4 | Tween 80 | 1000 | 100 | 2.78 | 0.84 |
| 5 | Tween 80 | 1000 | 10 | 6.33 | 1.49 |
| 6 | Tween 20 | 1000 | 100 | 24.4 | 15.7 |
| 7 | Tween 20 | 1000 | 10 | 4.76 | 3.34 |

*Independent determination

These data suggest that formulations prepared by dissolving triacontanol in organic solvents and then mixing with water to precipitate triacontanol particles typically have a large mean particle size and undergo rapid flocculation.

What is claimed is:

1. A stable colloidal dispersion comprising:
   (a) from about $10^{-10}$ g/l to about 0.5 g/l of 1-triacontanol having a mean particle radius of less than about 0.3 microns, and
   (b) water.

2. A dispersion according to claim 1 comprising from about $10^{-8}$ g/l to about 0.4 g/l of 1-triacontanol.

3. A dispersion according to claim 2 comprising from about $10^{-5}$ g/l to about 0.25 g/l of 1-triacontanol.

4. A dispersion according to claims 1 or 3 wherein the 1-triacontanol has a mean particle radius of less than about 0.25 microns.

5. A dispersion according to claim 4 wherein the 1-triacontanol has a mean particle radius of less than about 0.15 microns.

6. A stable colloidal dispersion comprising:
   (a) from about $10^{-10}$ g/l to about 4 g/l of 1-triacontanol having a mean particle radius of less than about 0.3 microns,
   (b) a dispersing agent selected from the group consisting of anionic, cationic, zwitterionic and polyfunctional single bond nonionic surfactants, wherein the dispersing agent is present at a concentration of less than about 50% by weight of the 1-triacontanol and, additionally, is present at a concentration less than its critical micelle concentration when it has a hydrocarbyl chain length of less than or equal to about 18 carbon atoms, and (c) water.

7. A dispersion according to claim 6 comprising from about $10^{-8}$ g/l to about 3 g/l of 1-triacontanol.

8. A dispersion according to claim 7 comprising from about $10^{-5}$ g/l to about 1.5 g/l of 1-triacontanol.

9. A dispersion according to claims 6 or 8 wherein the 1-triacontanol has a mean particle radius of less than about 0.25 microns.

10. A dispersion according to claim 9 wherein the 1-triacontanol has a mean particle radius of less than about 0.15 microns.

11. A dispersion according to claim 6 wherein the dispersing agent is present at a concentration of less than about 20% by weight of the 1-triacontanol.

12. A dispersion according to claim 11 wherein the dispersing agent is present at a concentration of less than about 2% by weight of the 1-triacontanol.

13. A dispersion according to claim 6 wherein the dispersing agent has a hydrocarbyl chain length of less than or equal to about 18 carbon atoms and is present at a concentration of less than about 0.25 times its critical micelle concentration.

14. A dispersion according to claim 13 wherein the dispersing agent is present at a concentration of less than about 0.1 times its critical micelle concentration.

15. A dispersion according to claim 6 wherein the dispersing agent is selected from the group consisting of sodium or potassium $C_{14}$–$C_{24}$ alkyl sulfates, alkyl ether ethoxylate sulfates containing less than about 2 ethylene oxide units, alkyl glyceryl ether sulfonates and fatty acid soaps.

16. A dispersion according to claim 15 wherein the dispersing agent is sodium tallow alkyl sulfate.

17. A dispersion according to claim 16 comprising from about $10^{-5}$ g/l to about 1.5 g/l of 1-triacontanol having a mean particle radius of less than about 0.15 microns, and wherein the sodium tallow alkyl sulfate is present at a concentration less than about 0.1 times its critical micelle concentration.

18. A dispersion according to claims 1, 6 or 17 wherein the 1-triacontanol is greater than about 97% pure.

19. A dispersion according to claim 18 wherein the 1-triacontanol is greater than about 99% pure.

20. A dispersion according to claims 1 or 6 additionally comprising up to about 40% by weight of an antifreeze material.

21. A dispersion according to claim 20 wherein the antifreeze material is propylene glycol.

22. A dispersion according to claim 21 comprising from about 10% to about 25% by weight of the propylene glycol.

23. In the method for stimulating the growth of a plant by applying to the plant an effective amount of triacontanol, the improvement comprising applying triacontanol as a colloidal dispersion according to claim 1, 6 or 17; whereby a more consistent plant growth stimulation is obtained.

24. A method according to claim 23 wherein the dispersion is applied at a rate which provides from about $10^{-6}$ to about 1 g/ha of 1-triacontanol.

25. A method according to claim 24 wherein the dispersion is applied at a rate which provides from about $10^{-5}$ to about $10^{-2}$ g/ha of 1-triacontanol.

* * * * *